US 6,733,769 B1

(12) United States Patent
Ryan et al.

(10) Patent No.: US 6,733,769 B1
(45) Date of Patent: May 11, 2004

(54) METHODS FOR LOWERING VISCOSITY OF GLUCOMANNAN COMPOSITIONS, USES AND COMPOSITIONS

(75) Inventors: Valerie J. Ryan, Boston, MA (US); Chienkuo Ronnie Yuan, Chelmsford, MA (US); Guy A. Crosby, Weston, MA (US)

(73) Assignee: Opta Food Ingredients, Inc., Bedford, MA (US)

( * ) Notice: Subject to any disclaimer, the term of this patent is extended or adjusted under 35 U.S.C. 154(b) by 0 days.

(21) Appl. No.: 09/306,530

(22) Filed: May 6, 1999

(51) Int. Cl.[7] .................. A61K 47/00; A61K 31/715; A23L 1/06; A23L 1/05
(52) U.S. Cl. .................. 424/439; 514/54; 514/58; 426/573; 426/575
(58) Field of Search .................. 514/54, 58; 426/573, 426/575; 424/439

(56) References Cited

U.S. PATENT DOCUMENTS

| | | | |
|---|---|---|---|
| 4,427,704 A | 1/1984 | Cheney et al. | 426/574 |
| 4,582,714 A | 4/1986 | Ford et al. | 426/564 |
| 4,720,389 A * | 1/1988 | Clare et al. | 426/329 |
| 4,746,528 A | 5/1988 | Prest et al. | 426/573 |
| 4,844,922 A | 7/1989 | Uemura et al. | 426/104 |
| 4,894,250 A | 1/1990 | Musson et al. | 426/573 |
| 5,308,636 A | 5/1994 | Tye et al. | 426/573 |
| 5,603,976 A | 2/1997 | Share et al. | 426/574 |
| 5,709,896 A * | 1/1998 | Hartigan et al. | 426/103 |
| 5,733,593 A | 3/1998 | Shelso et al. | 426/550 |
| 6,048,564 A * | 4/2000 | Young et al. | 426/573 |

FOREIGN PATENT DOCUMENTS

| | | |
|---|---|---|
| EP | 0 185 511 A | 6/1986 |
| EP | 0 898 900 A2 | 3/1999 |
| WO | WO 90/15544 | 12/1990 |

OTHER PUBLICATIONS

CA abstract, AN 1996:115286, Okui et al. 1996.*
Crosby, G., "Nutritional Flour Power", *Ingredients Health & Nutrition*, 5: (1999).
A. Arvill and L. Bodin, "Effect of Short–term Ingestion of Konjac Glucomannan on Serum Cholesterol in Healthy Men", *Am. J. Clin. Nutr.*, 61:585–599 (1995).
Jenkins et al., "Dietary Fibres, Fibre Analogues, and Glucose Tolerance: Importance of Viscosity", *British Medical Journal 1:1392–1394* (May 27, 1978).
Yoshimura et al., "Effects of Konjac–Glucomannan on the Gelatinization and Retrogradation of Corn Starch As Determined by Rheology and Differential Scanning Calorimetry", *J. Agric. Food Chem*, 44(10):2970–2976 (1996).
Ide et al., "Contrasting Effects of Water–Soluble and Water–Insoluble Dietary Fibers on Bile Acid Conjugation and Taurine Metabolism in the Rat", *Lipids*, 25(6):335–340 (1990).
Nutricol® Konjac, FMC (1994).

(List continued on next page.)

*Primary Examiner*—Shengjun Wang
(74) *Attorney, Agent, or Firm*—Hamilton, Brook, Smith & Reynolds, P.C.

(57) ABSTRACT

Methods of producing low viscosity glucomannan compositions by mixing a viscosity lowering compound with glucomannan under conditions suitable to form a low viscosity glucomannan composition are disclosed. The ability to modulate (increase or decrease) viscosity by combining glucomannan with compounds of differing molecular weights is described. Also, methods for lowering blood glucose and cholesterol in mammals by administering an effective therapeutic amount of maltodextrin-glucomannan complex are described. Additionally, methods for converting a food or beverage product from an initial low viscosity substance to a high viscosity end-product are also described herein.

23 Claims, 3 Drawing Sheets

OTHER PUBLICATIONS

LaBell, F., "Flour from Oriental Root Yields Heat–Stable Gels, Provides High Viscosity", *Food Processing*, Nov. 1989.

Tye, R., "Konjac Flour: Properties and Applications", *Food Technology*, Mar. 1991.

S.E. Davis and B.A. Lewis, "Physiological Effects of Mannans, Galactomannans, and Glucomannans", *Physiological Effects of Food Carbohydrates*, 296–311 (1975).

Shimisu H. et al., "Effects of Dietary Konjac Mannan on Serum and Liver Cholesterol Levels and Biliary Bile Acid Composition in Hamsters", *J. Pharmacobio–Dyn.*, 14:371–375 (1991).

Doi, K., "Effect of Konjac Fibre(glucomannan) on Glucose and Lipids", *European Journal of Clinical Nutrition*, 49(3):S190–S197 (1995).

"Physiological Active Glucomannan Drink Mix Glucomannan Granule Water Liquefy Obtain Konjak Paste Enzyme Heat Sterile", *Database WPI*, 323042 (1993) (Japan Patent Abstract: JP5199856).

* cited by examiner

METHODS FOR LOWERING VISCOSITY OF GLUCOMANNAN COMPOSITIONS, USES AND COMPOSITIONS

BACKGROUND OF THE INVENTION

Starch and hydrocolloid mixtures are often employed to modify and control the texture of food products. It has been well established that the addition of hydrocolloids increases the viscosity of starch. Konjac flour interacts synergistically with hydrocolloids such as κ-carrageenan, as well as other hydrocolloids in modifying the texture of food products. Yoshimura, M., et al., *J. Agric. Food Chem.*, 44:2970 (1996).

Konjac flour is produced from the tuber of the plant *Amorphopallus konjac*. Konjac flour contains a high molecular weight glucomannan polysaccharide consisting of mannose and glucose in a molecular ratio of approximately 3:2 respectively, with beta-1,4-linkages. The molecular weight is greater than 300,000 daltons. Hydroxyl groups are present throughout the molecule providing some hydrophilicity, thereby imparting water solubility. Acetyl groups are important in controlling the gelling mechanism, but not critical in water solubility.

Konjac flour has several properties that can be readily used in food formulations. When konjac flour is mixed with water, the small sacs containing the flour swell as they absorb the water. The viscosity of the dispersion begins to increase as the sacs swell with water and release the konjac flour. Konjac has a high capacity for water absorption. Tye, R. J., *Food Technology*, 45(3):82–92 (March 1991). Therefore, the addition of konjac flour may alter the viscosity of the preparation. Konjac flour may be used with starch, with or without other gums or stabilizers present. Generally, as the concentration of konjac increases in the presence of many starches there is a concomitant increase in the viscosity of the dispersion mixture. Konjac flour functionally interacts with most starches to give a considerable increase in viscosity that is maintained during cooking and cooling. Tye (March 1991).

Another attractive feature of konjac is its thermal stability. Generally, gels formed by polysaccharides other than konjac will lose their network structure at high temperatures. Konjac is different in that it can maintain its network lattice even at relatively high temperatures while other polymers will lose their gel structure at these same temperatures. Tye (March 1991).

Dietary fiber has been suggested as an effective food ingredient in the prevention of such diseases as diabetes, hyperlipidemia, coronary heart disease, colon diverticulum and colon cancer. The reason ascribed to fiber's efficacy is the high viscosity that it possesses. Jenkins, D. J. A., et al., *British Med. J.*, 1:1392 (1978). Recent studies suggest that a high-fiber diet in conjunction with konjac flour as a supplement confers a beneficial effect on lipid and glucose levels that actually might retard or prevent the formation of atherosclerosis in a diabetic patient. Doi, K., *Eur. J. Clin. Nutr.*, 49, Suppl. 3:190 (1995). Arvill and Bodin examined the effects of soluble fiber konjac on serum cholesterol in adult human males. The results of their study show that konjac is an effective cholesterol lowering dietary adjunct. Arvill, A. and L. Bodin, *Am. J. Clin. Nutr.*, 61:585–589 (1995).

SUMMARY OF THE INVENTION

The present invention pertains to compositions and methods of making a low viscosity glucomannan (e.g., konjac) composition comprising glucomannan and a viscosity lowering compound, such as polysaccharides (e.g., maltodextrin, inulin and hydrolyzed guar gum) and proteins, present in amounts that when dispersed in an aqueous medium results in a low viscosity glucomannan dispersion, compared to a glucomannan dispersion without the viscosity lowering compound present.

The present invention also pertains to methods of making a low viscosity glucomannan composition comprising dispersing a viscosity lowering compound with glucomannan (e.g., konjac) in an aqueous medium to form a low viscosity dispersion resulting from the interaction of the two components.

In one embodiment of the invention, the glucomannan is konjac flour and the viscosity lowering compound is the polysaccharide maltodextrin. In this embodiment, maltodextrin and konjac are heated to a temperature sufficient to disperse the two components in an aqueous medium. The viscosity of the dispersion significantly drops to yield a low viscosity composition resulting from the interaction of the two components.

In another embodiment of the invention, the viscosity lowering polysaccharide can be maltodextrin, hydrolyzed guar gum, inulin or combinations thereof. One or more of these viscosity lowering compounds are dispersed in an aqueous medium with glucomannan (e.g., konjac) to form a low viscosity dispersion resulting from the interaction of the components of the dispersion. The presence of hydrolyzed guar gum and/or inulin also provides a source of dietary fiber.

The konjac compositions of the present invention can be used to stabilize or texturize food and beverage products, such as in the production of ice cream, and as a fat substitute in a variety of reduced fat, low fat and fat free foods and beverages, such as cakes, pudding type desserts, butter, peanut butter, salad dressings, sauces, margarine, cream cheese and other spreads, snack dips, mayonnaise, sour cream, yogurt, ice cream, frozen desserts, fudge and other confections, and skim milk. The konjac compositions can be incorporated into fat free, reduced fat, low fat and fat containing cheeses, such as natural, processed and imitation cheeses in a variety of forms (e.g., shredded, block, slices and grated). The konjac compositions are also useful, as for example, a shortening, in baked goods such as cakes, pies, brownies, cookies, breads, noodles, snack items, such as crackers, graham crackers and pretzels, and similar products.

The ability to modulate (i.e., increase or decrease) the viscosity of the compositions of the invention is advantageous in the preparation of food products and beverages. In another embodiment of the invention, a method for preparing a high viscosity food product and beverage from a low viscosity starting preparation is described. A combination, for example, of a high use level of konjac and low dextrose equivalent value (hereinafter "DE") maltodextrin can be used in systems that require a low process viscosity, such as spray drying or filling operation. Subsequent hydrolysis of the maltodextrin, such as by using α-amylase or acid hydrolysis, in the mixture will result in the increase of viscosity in the product.

Since konjac has been shown to beneficially affect lipid and glucose levels, the compositions of this invention can be used as therapeutic agents therefor. Accordingly, the invention pertains to a method for lowering blood glucose in a mammal, including human, in need thereof by administering an effective therapeutic dose of the compositions described herein to a mammal in order to reduce the blood glucose level.

In another aspect of the invention, the compositions of this invention can be administered to a mammal, including human, for the purpose of lowering blood cholesterol levels.

DETAILED DESCRIPTION OF THE INVENTION

Figure 1:
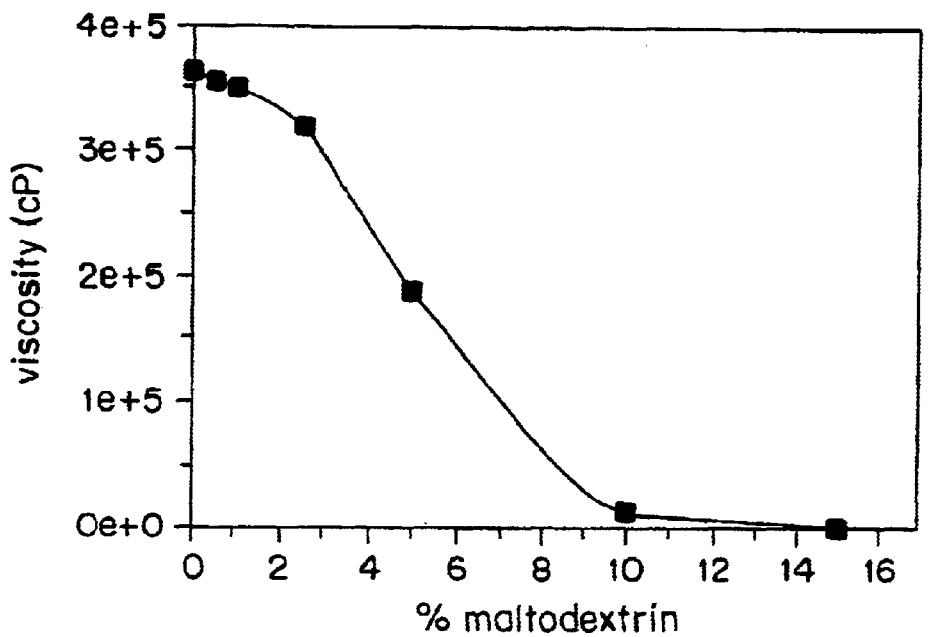
FIG. 1 illustrates the effect of increasing maltodextrin concentration, with DE held constant, on viscosity of 2% konjac dispersion.

The invention is based upon the discovery that certain compounds such as polysaccharides like maltodextrin, hydrolyzed guar gum and inulin, and certain proteins, have the ability to lower the viscosity of glucomannan solutions. This phenomenon is dependent on the amount and the molecular weight of, for example, the polysaccharide employed. For example, the ratio of maltodextrin to glucomannan has an inverse relationship on viscosity, that is, increasing use levels of maltodextrin causes the viscosity to decrease. Maltodextrin DE values directly affect viscosity, that is, as the DE value decreases so does the viscosity, this represents an inverse relationship in terms of molecular weight (i.e., low DE corresponds to a high molecular weight). This discovery has now made it possible to formulate compositions containing high use levels of glucomannan, such as nutritional beverages, which could not have been heretofore made because glucomannans are known to form extremely viscous solutions that are unsuitable for beverage manufacture. This phenomenon is also in contrast to the viscosity building synergy reported for starch and glucomannan (e.g., konjac) formulations. Tye, R. J., *Food Technology*, 45(3):82–92 (March 1991).

Glucomannan compositions of this invention comprise glucomannan and a viscosity lowering compound. The composition has a lower viscosity compared to similar glucomannan composition absent the viscosity lowering compound. Glucomannan can be extracted from the Amorphopallus species, for example, *A. riviera* and its varieties (often referred to as *A. konjac*), *A. oncophyllus, A. varialis, A. bulbifera* and *A. blumeli*. The preferred glucomannan from an Amorphopallus species is commonly referred to as konjac flour (or yam flour). For simplicity, the term "konjac" will be used in the discussion of the invention but its use is illustrative of a preferred embodiment of the class of glucomannans.

A "viscosity lowering compound" as the term is used herein is intended to embrace polysaccharides and proteins which when added to a glucomannan dispersion can lower the viscosity of that dispersion. Examples of viscosity lowering polysaccharides include lower molecular weight polysaccharides such as maltodextrin, inulin and hydrolyzed guar gum. Compounds, specifically effective polysaccharides, having a viscosity lowering effect have been shown to fall within a representative molecular weight range of about 1000 to about 50,000 Daltons. These values refer to an approximate molecular weight range with values falling above and below the given range. The viscosity lowering effect of these compounds is in contrast to the known effects larger molecular weight compounds have in increasing viscosity. Tye, R. J., *Food Technology*, 45(3):82–92 (March 1991).

Maltodextrin is a product obtained from the hydrolysis of starch. It has a DE of less than 20. Low DE maltodextrins are more effective in decreasing the viscosity of konjac. The term DE reflects the degree of polymerization. Low DE maltodextrin refers to a relatively long chain length species of maltodextrin. Generally, low DE maltodextrins decrease the viscosity of konjac, however upon hydrolysis, using, for example, enzymatic or acid-mediated hydrolysis, of a low DE maltodextrin, the maltodextrin-konjac product will increase in viscosity. In a preferred embodiment, the viscosity lowering compound is maltodextrin, having a DE value less than about 18. See U.S. Pat. No. 4,746,528 to Prest, C. T., et al.; the entire teachings of which are incorporated herein by reference. Preferably, the amount of maltodextrin employed can be from about 0.5% to about 20% by weight of solution. See Example 1.

Generally, a low viscosity glucomannan composition is produced by admixing glucomannan and a viscosity lowering compound in an aqueous medium under conditions sufficient to form a glucomannan composition low in viscosity, compared to a glucomannan composition absent the viscosity lowering compound, such as a polysaccharide.

A maltodextrin-konjac composition can be produced by heating maltodextrin in the presence of konjac and an aqueous medium (e.g., water) under conditions sufficient to hydrate the konjac and solubilize the maltodextrin. Examples of an aqueous medium include, but are not limited to, water, milk, water-based beverages, milk-based beverages, carbonated beverage, non-carbonated beverage, fruit-based beverage, beer, wine and soy milk. There exists at least three different orders of dispersion for the two ingredients in preparing a maltodextrin-konjac composition. The ingredients can be added simultaneously (e.g., as a dry blend of glucomannan and viscosity lowering polysaccharide) or sequentially (e.g., viscosity lowering polysaccharide followed by glucomannan, and the reverse thereof) to the aqueous medium. The three methods of dispersion all result in lowering viscosity but each will yield a product with somewhat different properties distinguishable from each other. The method of dispersion suitable should be chosen based on the application and the desired properties and/or end uses.

Briefly, the differences in the three protocols are presented below. For simultaneous addition of ingredients, a dry blend of the two ingredients is formed. This dry blend can be dispersed into approximately from about 70° C. to about 80° C. water with stirring or mixing. For preparing a viscosity lowering polysaccharide and then glucomannan dispersion, the viscosity lowering polysaccharide can be dispersed into approximately from about 70° C. to about 80° C. water with stirring or mixing. The konjac can be added as a dry powder to the dispersion with stirring or mixing. The third dispersion method, that is, glucomannan and then viscosity lowering polysaccharide, involves the dispersion of glucomannan in water approximately from about 70° C. to about 80° C. with stirring or mixing to hydrate. The viscosity lowering polysaccharide is next added to the dispersion with stirring or mixing.

The amount of glucomannan incorporated into the compositions of the invention will depend, in part, upon the degree of viscosity, the type of product in which the composition will be incorporated, and the amount of glucomannan intended to be consumed, particularly in the instance where the final product is used for nutritional or therapeutic benefit (e.g., an amount sufficient (approximately from about 3 g/day to about 10 g/day) to decrease serum cholesterol and/or glucose). Most preferably, from about 0.5% to about 5.0% by weight konjac is used. Preferably, maltodextrin is added to a heated aqueous medium at a temperature of from about 70° C. to about 80° C. and in an amount of from about 0.5% to about 20% by weight. Konjac flour is then added at a level of from about 0.5% to about 5.0% by weight to maltodextrin in solution, however, the amount of konjac and maltodextrin used will depend upon end use and/or processing needs of the resultant maltodextrin-konjac composition.

Alternatively, employing maltodextrin at a particular DE value can be used to modulate konjac viscosity. Maltodextrin with a DE value about less than 18 is a preferred maltodextrin preparation. See Example 2.

In another alternative, a preparation of maltodextrin can be added to a dry blend of konjac. This mixture is then hydrated. First, a dry blend of the two ingredients is formed. The dry blend is dispersed in from about 70° C. to about 80° C. water with stirring or mixing.

Maltodextrin was examined for use with non-glucomannan hydrocolloids in creating low viscosity dispersions. Specifically, guar gum was examined in combination with maltodextrin to determine whether there was a decrease in viscosity of the dispersion. The combination of guar gum and maltodextrin did not demonstrate any significant decrease in the viscosity of the dispersion. See Example 3.

In one embodiment of the invention, a non-maltodextrin polysaccharide is mixed with konjac to produce a low viscosity dispersion. Konjac is added to a hydrolyzed guar, an example of a non-maltodextrin polysaccharide, solution using an overhead mixer. The hydrolyzed guar is pre-dispersed at a level of from about 1% to about 20% by weight in from about 70° C. to about 80° C. water with stirring. The final konjac level is approximately 1% and the final hydrolyzed guar level is about 10%. See Example 4.

In another embodiment of the invention, a non-maltodextrin polysaccharide is mixed with konjac to produce a low viscosity dispersion. Konjac is added to inulin, an example of a non-maltodextrin polysaccharide, solution using an overhead mixer. The inulin is pre-dispersed at a level of from about 1% to about 30% by weight in from about 70° C. to about 80° C. water with stirring. The final konjac level is approximately 1% and the final inulin level is about 15%. See Example 5.

In still another embodiment of the instant invention, a combination of polysaccharides are mixed with konjac in order to produce a low viscosity dispersion. The polysaccharides that can be combined and mixed with konjac include maltodextrin, hydrolyzed guar gum and inulin. The mixture can contain two or more of these polysaccharides mixed in various proportions with one another (e.g., if only two polysaccharides are mixed together, they can be mixed using a 50:50 ratio, other combinatorial ratios are encompassed within this invention). Preferably, only two of the polysaccharides are mixed together before mixing with konjac. The polysaccharide is pre-dispersed at a level of from about 1% to about 30% by weight in from about 70° C. to about 80° C. water with stirring. The final konjac level is approximately 1% and the final polysaccharide level is from about 10% to about 15%.

Konjac can be delivered as a food or beverage in a combination with maltodextrin in order to modify the viscosity of the food or beverage product. This is particularly desirable when there is a need to have a low viscosity preparation of which konjac is an ingredient. Such is the case when it is necessary to have high levels of konjac in a viscosity-sensitive system.

The low viscosity konjac compositions produced by methods described herein are useful in a variety of food and beverage applications. In particular, a konjac composition, which is produced by methods described herein, can be used as an ingredient in many food and beverage products. The ability to modify the viscosity of a konjac-incorporated viscosity-sensitive system by changing to a maltodextrin with a different DE provides greater flexibility in food formulations without altering the carbohydrate level. Alternatively, viscosity can be modified by changing the ratio of konjac to maltodextrin. The amount of maltodextrin used is from about 0.5% to about 20% by weight. The DE value for maltodextrin used is less than about 18. High levels of konjac can be used in food and beverage products while maintaining a relatively low viscosity. This characteristic together with konjac's ability to enhance water retention allows konjac to serve as a fat mimetic. This ability to employ high levels of konjac has health related consequences, such as lowering blood glucose and cholesterol levels in mammals, including humans. Konjac dispersion at high use levels is now possible using typical laboratory or industrial plant equipment.

The konjac compositions of the present invention can be used to stabilize or texturize food and beverage products, such as in the production of ice cream, and as a fat substitute in a variety of reduced fat, low fat and fat free foods, such as cakes, pudding type desserts, sauces, margarine, butter, peanut butter, cream cheese and other spreads, salad dressings, snack dips, mayonnaise, sour cream, yogurt, ice cream, frozen desserts, fudge and other confections, and skim milk. The konjac compositions can be incorporated into fat free, low fat, reduced fat and fat-containing foods like cheeses, such as natural, processed and imitation cheeses in a variety of forms (e.g., shredded, block, slices and grated) (U.S. Pat. No. 5,603,976; the entire teachings of which are incorporated herein by reference). The konjac compositions are also useful, as for example a shortening in baked goods such as cakes, pies, brownies, cookies, breads, noodles, snack items, such as crackers, graham crackers and pretzels, and similar products, as it does not interfere with the organoleptic properties of the foods in which it is incorporated.

The terms "fat free", "low fat" and "reduced fat" as used herein are intended to embrace the definitions set forth by the Nutrition Labeling and Education Act (NLEA), Federal Register, Jan. 6, 1993.

The konjac compositions of the invention allow for a conversion from low to a high viscosity system that can be used in nutritional beverages or gels, such as in sports gels.

This conversion process is important for systems in which low viscosity is initially required followed by a high viscosity end point.

A konjac preparation can be mixed with maltodextrin under conditions suitable to produce a maltodextrin-konjac dispersion possessing low viscosity. In a preferred embodiment, the maltodextrin used has a dextrose equivalent value that is less than about 18. Preferably, the konjac preparation is formed by employing from about 0.5% to about 5.0% by weight konjac flour which can be added to a suitable medium, such as a phosphate buffer. This low viscosity maltodextrin-konjac dispersion can be subjected to hydrolysis (e.g., enzymatic and/or acid hydrolysis). This hydrolysis results in the decrease of molecular weight for maltodextrin, thereby producing a high viscosity food or beverage product. The hydrolysis of the maltodextrin-konjac composition involves the hydrolysis of maltodextrin to glucose. The hydrolysis of maltodextrin can be facilitated by employing an enzyme, such as α-amylase. The konjac composition can be incubated in the presence of α-amylase under conditions and time sufficient to hydrolyze the maltodextrin to the extent that it no longer suppresses the viscosity of the konjac. Hydrolysis of maltodextrin can also be accomplished by subjecting the composition to acid hydrolysis using an appropriate acidic pH, such as pH 4.5 or below. Cleavage of the maltodextrin can occur in situ where the acidic pH (approximately pH 2.0–4.5) of the upper gastrointestinal tract is sufficient to cleave the linkages between the glucose molecules in maltodextrin and convert the dispersion from a low to high viscosity substance. A combination of both hydrolysis methods, i.e., enzymatic and acid hydrolysis, can also be used in order to liberate konjac from the influence of the maltodextrin molecule.

As illustrated in the Examples, a konjac dispersion can be prepared by adding from about 0.5% to about 5.0% by weight of konjac flour to a phosphate buffer solution (from about pH 6.7 to about pH 7.2) at room temperature and stirring for approximately 30 minutes. A maltodextrin solution is prepared by dissolving a sufficient amount of maltodextrin with a DE less than 18 into a phosphate buffer solution (from about pH 6.7 to about pH 7.2). The maltodextrin solution is heat-agitated until the solution appears clear. The maltodextrin solution is then mixed with the konjac preparation using an overhead mixer. The combined dispersion is cooled to about 37° C. in a water bath. The resultant dispersion is a low viscosity maltodextrin-konjac composition.

The low viscosity dispersion is then subjected to enzymatic treatment. A sufficient amount of α-amylase, for example, is added to the low viscosity maltodextrin-konjac dispersion. A sufficient amount of enzyme is that which contains the appropriate enzymatic Units necessary to hydrolyze the maltodextrin to glucose, specifically in this case, the α1–4 glycosidic bond in the maltodextrin. The enzyme-treated sample is incubated at about 37° C. in a water bath for a time sufficient to effectuate cleavage of the glycosidic linkage that reduces the molecular weight of the maltodextrin resulting in a high viscosity product. In addition to enzymatic cleavage, the present invention encompasses other well known protocols for cleaving glycosidic linkages present in maltodextrin known to those skilled in the art, for example, acid hydrolysis employing acids like HCl at a pH of about less than 4.5. See Example 6.

The konjac composition can be delivered more as a traditional pharmaceutical, for example, in a nutritional beverage or gelatin capsule, rather than as a food or beverage. A nutritional beverage is that which provides a nutritional level of about 3.0 g/day to about 10 g/day (e.g., single or multiple servings per day). A nutritional beverage containing konjac can be used to lower, for example, blood glucose levels, serum cholesterol and low density lipid protein cholesterol. The important aspect to delivering konjac in the form of a konjac composition is that viscosity can be modified which allows for greater flexibility in the delivery of konjac. For example, it may be desirable to deliver a low viscosity preparation of viscosity lowering compound and konjac with the goal of converting to a high viscosity end point active agent (in this case it is glucomannan) which would be present in the gastrointestinal tract.

Recent studies have demonstrated the effectiveness of glucomannan in lowering serum glucose and cholesterol in humans. Arvill, A. and Bodin, L., *Am. J. Clin. Nutr.*, 61:585–589 (1995); Doi, K., *Eur. J. of Clin. Nutr.*, 49, suppl. 3:S190–S197 (1995); and Shimizu, H., et al., *J. Pharmacobio-Dyn.*, 14:371–375 (1991). A potential difficulty in adopting glucomannan in a therapeutic regime is the viscosity that is generally associated with levels considered to be therapeutic in the treatment of certain disease processes, such as diabetes. There exists a need to deliver a low-viscosity glucomannan preparation if it is to be considered as a realistic therapeutic approach to diseases like hypercholesteremia and diabetes. One approach used to address this problem of delivering a low-viscosity composition to patients, for example, diabetes patients, is described in EP 0 898 900 A2 to Societe Des Produits Nestle S. A., the entire teachings of which are herein incorporated by reference. In this approach, a composition comprising a protein source, a lipid source and a carbohydrate source, wherein the carbohydrate source includes a fiber mixture containing a viscous soluble fiber and inulin is employed. In liquid form this preparation has a low viscosity.

The present invention also pertains to a method for lowering blood glucose levels in a mammal, including human, comprising administering to the mammal an effective therapeutic amount of the konjac composition. In a study conducted on diabetic patients, the therapeutic effects of konjac were analyzed in this group of patients. A total of 195 patients with diabetes participated in the study. They were grouped according to the type of treatment they were receiving. All of the patients took 7.8 grams of glucomannan daily for sixteen weeks. The results of the study found a significant reduction in blood glucose levels in those patients tested. Doi, K., et al., *Progress in Obesity Research* 1990. *Proceedings of the Sixth International Congress on Obesity*, eds. Oomura, Y., et al., Pub. John Libbey (London), pp 507–514 (1990).

In addition to lowering blood glucose levels, the present invention pertains to a method for lowering blood cholesterol in a mammal, including human, comprising administering to the mammal an effective therapeutic amount of the konjac composition. In the study referenced above by Doi et al., the blood cholesterol was examined using these same patients. The study revealed that the mean cholesterol level in the participating patients, both obese and non-obese, was reduced in those consuming glucomannan daily. Doi, K., et al., *Progress in Obesity Research* 1990. *Proceedings of the Sixth International Congress on Obesity*, eds. Oomura, Y., et al., Pub. John Libbey (London), pp 507–514 (1990); also see Arvill, A. and Bodin, L., *Am. J. Clin. Nutr.*, 61:585–589 (1995).

It should be understood that although the present text is directed to maltodextrin-konjac dispersions, the konjac compositions serve an illustrative purpose and therefore, the principals contained herein may be applied to other viscosity lowering compounds.

The teachings of references referred to herein are incorporated herein by reference. All percentages are by total weight unless otherwise specified.

The following examples are offered for the purpose of illustrating the present invention and are not to be construed to limit the scope of the present invention:

EXAMPLES

Example 1

Effect of Maltodextrin Concentration on Viscosity of Konjac Dispersions

The effect of maltodextrin concentration, with maltodextrin DE held constant, on the viscosity of konjac dispersions was assessed. Konjac flour was added to increasing levels of DE 5 maltodextrin in solution. To prepare the sample, maltodextrin was stirred in approximately 70° C. water to form six solutions. Konjac powder was then stirred into each maltodextrin solution. The final konjac concentration was 2%. The final maltodextrin concentration in each of 6 different solutions was 0.0, 0.5, 1.0, 2.5, 5.0, 10.0, and 15.0%. Viscosity was determined using a Brookfield type viscometer at 2 rpm.

Results shown in FIG. 1 illustrate decreasing viscosity with increasing maltodextrin levels, or an inverse relationship of viscosity to maltodextrin concentration.

Example 2

Effect of Maltodextrin DE on Viscosity of Konjac Dispersions

The effect of maltodextrin DE value on konjac viscosity was evaluated. Maltodextrin with DE values ranging from 1–18 was stirred in approximately 70° C. to 80° C. water to form solutions (note: DE 1 maltodextrin is not fully soluble under these conditions). Konjac powder was then stirred into each maltodextrin solution. The final maltodextrin concentration was 10% and konjac was 3%. Viscosity was determined using a Brookfield type viscometer at 2 rpm.

Figure 2:
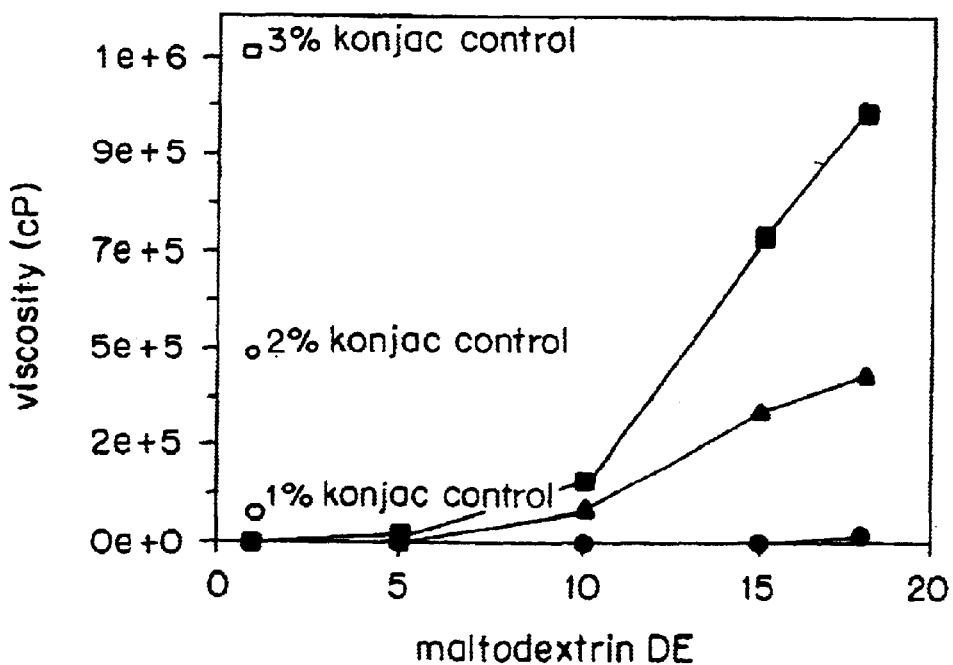
FIG. 2 illustrates the effect of varying maltodextrin DE values on viscosity of konjac dispersions. Konjac controls show the viscosity of konjac with no maltodextrin added. The effect is shown at three konjac to maltodextrin ratios. The shaded box represents 3% konjac plus 10% maltodextrin, the shaded triangle represents 2% konjac plus 11% maltodextrin and the shaded circle represents 1% konjac plus 12% maltodextrin.

FIG. 2 shows that the effect of reducing konjac viscosity increases when combined with maltodextrins having low DE values. This represents a direct relationship of viscosity to maltodextrin DE. At the same time, an inverse relationship of viscosity to maltodextrin molecular weight is represented. (The unshaded boxes represent konjac controls with no maltodextrin present at each concentration as noted on the graph). The effect is shown at three konjac to maltodextrin ratios.

Example 3

Effect of Maltodextrin on Guar Gum Dispersion

Figure 3:
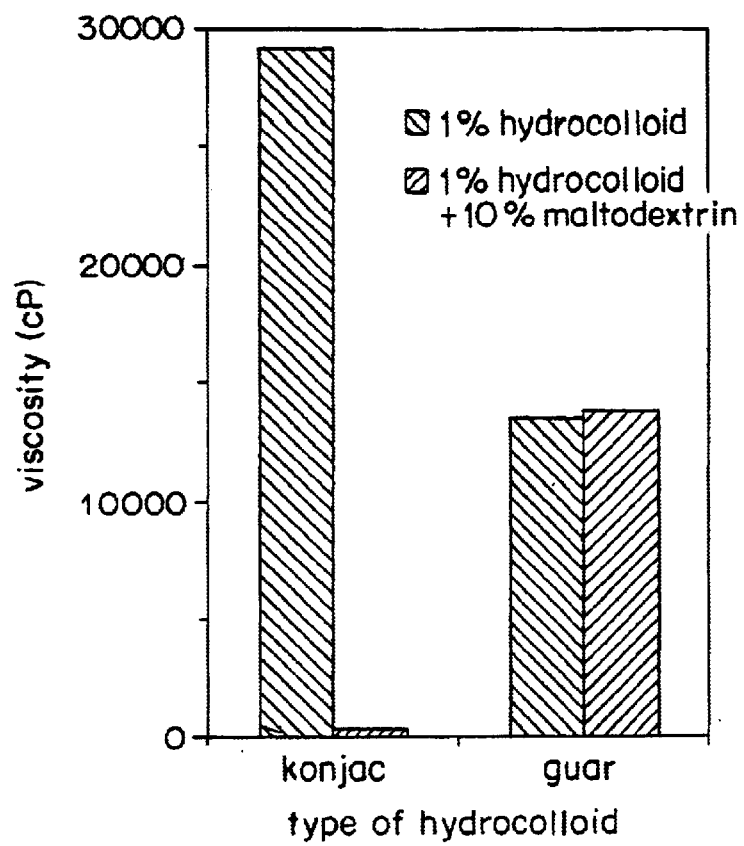
FIG. 3 illustrates the effect of maltodextrin on non-glucomannan hydrocolloids, where the shaded box represents 1% hydrocolloid and the hashed box represents 1% hydrocolloid plus 10% maltodextrin.

Guar gum was added with an overhead mixer to DE 5 maltodextrin pre-dispersed in approximately 70° C. water. The final guar gum concentration was 1% and the final maltodextrin concentration was 10%. Viscosity was monitored on a Brookfield type viscometer at 2 rpm. FIG. 3 indicates that maltodextrin does not decrease the viscosity of guar gum dispersions.

Example 4

Effect of Hydrolyzed Guar on Konjac Viscosity

To examine the effect of non-maltodextrin polysaccharides on konjac viscosity, hydrolyzed guar gum was used. Konjac was added to a hydrolyzed guar gum solution with an overhead mixer. The hydrolyzed guar was pre-dispersed in approximately 70° C.–80° C. water with stirring. The final konjac concentration was 1% and the final hydrolyzed guar concentration was 10%. Viscosity was determined on a Brookfield type viscometer at 60 rpm.

Figure 4:
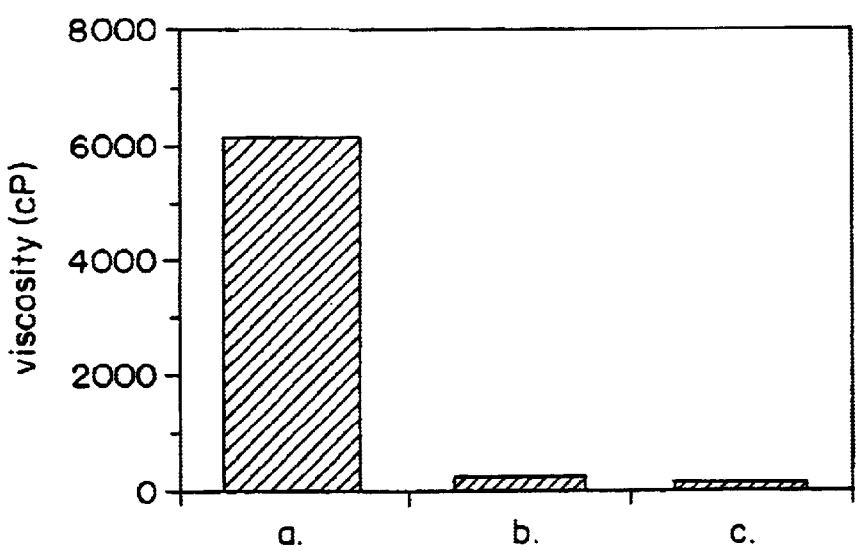
FIG. 4 illustrates the effect of hydrolyzed guar on konjac viscosity, where (a) is 1% konjac control, (b) is 1% konjac plus 10% maltodextrin and (c) is 1% konjac plus 10% hydrolyzed guar.

Results showed that the hydrolyzed guar decreases the viscosity of konjac dispersions as illustrated in FIG. 4. This indicates that non-maltodextrin polysaccharides also interact with konjac to reduce its viscosity.

Example 5

Effect of Inulin on Konjac Viscosity

To examine the effect of non-maltodextrin polysaccharides on konjac viscosity, inulin was used. Konjac was added to a inulin solution with an overhead mixer. The hydrolyzed guar was pre-dispersed in approximately 70° C.–80° C. water with stirring. The final konjac concentration was 1% and the final inulin concentration was 15%. Viscosity was determined on a Brookfield type viscometer at 60 rpm.

Figure 5:
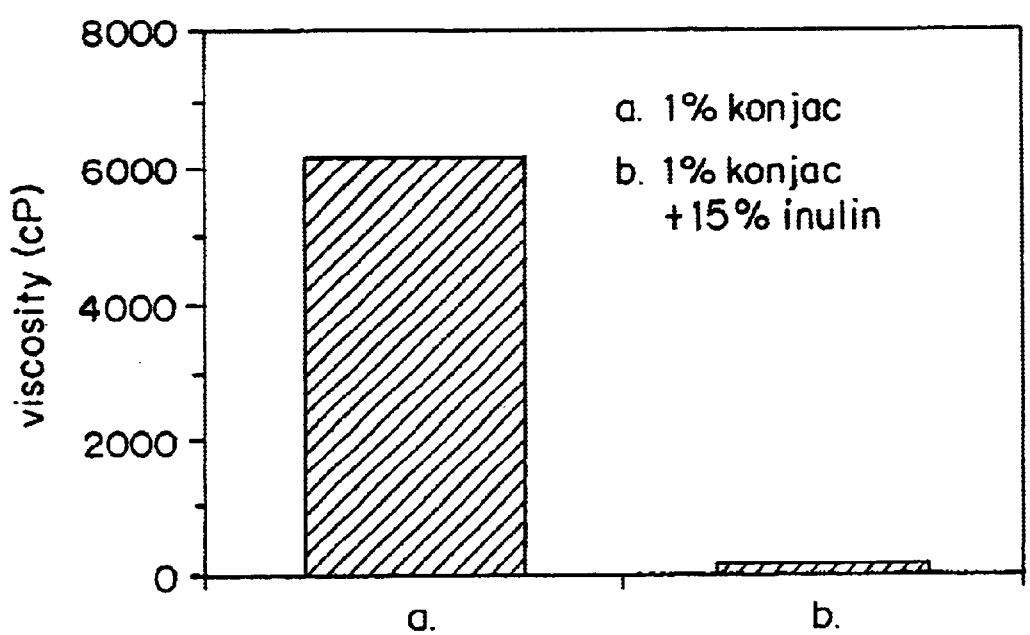
FIG. 5 illustrates the effect of inulin on konjac viscosity, where (a) is 1% konjac control, (b) is 1% konjac plus 15% inulin.

Results showed that the inulin decreases the viscosity of konjac dispersions as illustrated in FIG. 5, and is an example of the effect of a non-maltodextrin polysaccharide on konjac.

Example 6

Effect of Enzymatic Digestion

A konjac dispersion was prepared by adding 8 g of konjac flour to 392 g of 0.02 M phosphate buffer solution (pH 6.9) at room temperature for 30 minutes. A 400 g maltodextrin solution was prepared by dissolving 120 g of DE 5 maltodextrin in 280 g of buffer by heating at 70° C. under agitation until the solution turned clear. The maltodextrin solution was then combined with the previously prepared konjac dispersion using an overhead mixer. The combined dispersion was allowed to cool to 37° C. in a water bath.

The dispersion was divided into two 400 g portions. To one of the two portions was added 4 mL of porcine pancreatic α-amylase solution, which contains 3000 Units of activity per mL (Sigma Chemical Co., St. Louis, Mo.). To the other portion was added 4 mL of phosphate buffer as a control. The two samples were incubated in a 37° C. water bath for 24 hours. Viscosity of each sample was measured at time 0 (prior to enzyme addition) and at 1, 2 and 24 hours after enzyme addition using a Brookfield type viscometer at 60 rpm. TABLE 1 shows the viscosity development of the samples. The results indicate that the viscosity of a konjac system can be increased by hydrolyzing the maltodextrin with α-amylase.

TABLE 1

| | Viscosity (cP) Konjac dispersion | |
|---|---|---|
| Time | (−) enzyme | (+) enzyme |
| 0 | 58 | 58 |
| 1 hr | 73 | 4150 |

TABLE 1-continued

| | Viscosity (cP) Konjac dispersion | |
|---|---|---|
| Time | (−) enzyme | (+) enzyme |
| 2 hr | 80 | 5140 |
| 24 hr | 88 | 6817 |

Example 7

Use of Konjac Blends in Food Systems

A model of a milk based nutritional beverage containing konjac flour was developed. The formulation for the model is as follows:

| 1. | Konjac | 1% |
|---|---|---|
| 2. | DE 5 Maltodextrin | 14.5% |
| 3. | Chocolate syrup | 3.5% |
| 4. | Fructose | 1.0% |
| 5. | Skim milk | 80% |

Viscosity of the sample was determined using a Brookfield type viscometer at 60 rpm. A control sample of 1% konjac dispersion in milk was also measured, both values were compared to two commercially available, fiber containing, nutritional beverages. TABLE 2 and shows that the konjac combination allows high levels of konjac to be used in a nutritional beverage.

TABLE 2

| Sample | viscosity (cP) |
|---|---|
| konjac and maltodextrin in milk | 191 |
| konjac in milk | 8717 |
| commercial product 1 | 57 |
| commercial product 2 | 119 |

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A food product or beverage, comprising a glucomannan composition comprising glucomannan and an edible viscosity lowering polysaccharide having a molecular weight of from about 1,000 to about 50,000 daltons dispersed in an aqueous medium, wherein the glucomannan composition has a low viscosity compared to glucomannan dispersed in the aqueous medium in the absence of the viscosity lowering polysaccharide.

2. The food product or beverage of claim 1 which is a fat-containing food product and beverage.

3. The food product or beverage of claim 1 which is a reduced fat, low fat or fat free food product and beverage.

4. The food product or beverage of claim 3, wherein the reduced fat, low fat or fat free food product or beverage is selected from the group consisting of: ice cream, cakes, pudding desserts, sauces, margarine, butter, peanut butter, salad dressings, cream cheese, snack dips, mayonnaise, sour cream, yogurt, frozen desserts, fudge, cheese and skim milk.

5. The food product or beverage of claim 1 which is used as a shortening in the process of manufacturing a baked food product.

6. The food product of claim 5, wherein the baked food product is selected from the group consisting of: cakes, pies brownies, cookies, breads, noodles, crackers, graham crackers and pretzels.

7. The food product or beverage of claim 1, wherein said aqueous medium is selected from the group consisting of: water, milk, water-based beverage, milk-based beverage, carbonated beverage, non-carbonated beverage, fruit-based beverage, beer, wine and soy milk.

8. The food product or beverage of claim 1, wherein the viscosity lowering polysaccharide is maltodextrin, hydrolyzed guar gum, inulin and combinations thereof.

9. The food product or beverage of claim 8, wherein the dextrose equivalent value of maltodextrin is less than about 18.

10. The food product or beverage of claim 1, wherein the glucomannan is konjac flour.

11. The food product or beverage of claim 8, wherein the amount of maltodextrin is from about 0.5% to about 20% by weight.

12. The food product or beverage of claim 10, wherein the amount of konjac is from about 0.5% to about 5.0% by weight.

13. The food product or beverage of claim 8, wherein the amount of hydrolyzed guar is from about 1% to about 20% by weight.

14. A food product or beverage, comprising a glucomannan composition consisting essentially of glucomannan and an edible viscosity lowering polysaccharide having a molecular weight of from about 1,000 to about 50,000 daltons, present in an amount that when incorporated into the food or beverage will result in a low viscosity food product or beverage compared to its viscosity in the absence of the viscosity lowering polysaccharide.

15. The food product or beverage of claim 14, wherein the glucomannan is konjac flour.

16. The food product or beverage of claim 14, wherein the viscosity lowering polysaccharide is selected from the group consisting of: maltodextrin, hydrolyzed guar gum, inulin and combinations thereof.

17. The beverage of claim 14, wherein the beverage is selected from the group consisting of: milk, water-based beverage, milk-based beverage, carbonated beverage, non-carbonated beverage, fruit-based beverage, beer, wine and soy milk.

18. A pharmaceutical product or nutritional beverage, comprising a glucomannan composition comprising glucomannan and an edible viscosity lowering polysaccharide having a molecular weight of from about 1,000 to about 50,000 daltons dispersed in an aqueous medium, wherein the glucomannan composition has a low viscosity compared to glucomannan dispersed in the aqueous medium in the absence of the viscosity lowering polysaccharide.

19. A pharmaceutical product or nutritional beverage, comprising a glucomannan composition consisting essentially of glucomannan and an edible viscosity lowering polysaccharide having a molecular weight of from about 1,000 to about 50,000 daltons, present in an amount that when incorporated into the pharmaceutical product or beverage will result in a low viscosity pharmaceutical product or beverage compared to its viscosity in the absence of the viscosity lowering polysaccharide.

20. A food product or beverage, comprising a glucomannan composition comprising glucomannan and an edible viscosity lowering polysaccharide having a molecular weight of from about 1,000 to about 50,000 daltons dispersed in an aqueous medium, wherein the glucomannan composition has a low viscosity compared to glucomannan dispersed in the aqueous medium in the absence of the viscosity lowering polysaccharide, wherein the polysaccharide is selected from the group consisting of maltodextrin, guar gum, inulin and combinations thereof.

21. A food product or beverage, comprising a glucomannan composition consisting essentially of glucomannan and an edible viscosity lowering polysaccharide having a molecular weight of from about 1,000 to about 50,000 daltons, present in an amount that when incorporated into the food or beverage will result in a low viscosity food product or beverage compared to its viscosity in the absence of the viscosity lowering polysaccharide, wherein the polysaccharide is selected from the group consisting of maltodextrin, guar gum, inulin and combinations thereof.

22. A pharmaceutical product or nutritional beverage, comprising a glucomannan composition comprising glucomannan and an edible viscosity lowering polysaccharide having a molecular weight of from about 1,000 to about 50,000 daltons dispersed in an aqueous medium, wherein the glucomannan composition has a low viscosity compared to glucomannan dispersed in the aqueous medium in the absence of the viscosity lowering polysaccharide, wherein the polysaccharide is selected from the group consisting of maltodextrin, guar gum, inulin and combinations thereof.

23. A pharmaceutical product or nutritional beverage, comprising a glucomannan composition consisting essentially of glucomannan and an edible viscosity lowering polysaccharide having a molecular weight of from about 1,000 to about 50,000 daltons, present in an amount that when incorporated into the pharmaceutical product or beverage will result in a low viscosity pharmaceutical product or beverage compared to its viscosity in the absence of the viscosity lowering polysaccharide, wherein the polysaccharide is selected from the group consisting of maltodextrin, guar gum, inulin and combinations thereof.

* * * * *